United States Patent
Rankin

(10) Patent No.: US 8,192,295 B2
(45) Date of Patent: Jun. 5, 2012

(54) METHOD AND APPARATUS FOR EVALUATING A PUTT

(75) Inventor: David B. Rankin, Winston-Salem, NC (US)

(73) Assignee: Callaway Golf Company, Carlsbad, CA (US)

( * ) Notice: Subject to any disclaimer, the term of this patent is extended or adjusted under 35 U.S.C. 154(b) by 427 days.

(21) Appl. No.: 12/464,725

(22) Filed: May 12, 2009

(65) Prior Publication Data

US 2009/0280921 A1 Nov. 12, 2009

Related U.S. Application Data

(60) Provisional application No. 61/052,343, filed on May 12, 2008, provisional application No. 61/052,314, filed on May 12, 2008.

(51) Int. Cl.
*A63B 57/00* (2006.01)

(52) U.S. Cl. ........ 473/199; 473/131; 473/151; 473/266; 473/405; 434/252

(58) Field of Classification Search .................. 473/199, 473/266, 131, 151, 405; 434/252; 463/2, 463/3, 7, 36
See application file for complete search history.

(56) References Cited

U.S. PATENT DOCUMENTS

| | | | |
|---|---|---|---|
| 5,700,204 A | 12/1997 | Teder | |
| 6,113,504 A | 9/2000 | Kuesters | |
| 6,210,170 B1 * | 4/2001 | Sorensen et al. | 434/323 |
| 6,533,674 B1 | 3/2003 | Gobush | |
| 6,774,932 B1 | 8/2004 | Ewing et al. | |
| 7,220,187 B2 | 5/2007 | Schmidt et al. | |
| 7,255,649 B1 | 8/2007 | McConnell | |
| 7,347,780 B1 * | 3/2008 | Best | 463/37 |
| 7,892,080 B1 * | 2/2011 | Dahl | 463/10 |
| 2004/0214623 A1 * | 10/2004 | Takahashi et al. | 463/2 |
| 2005/0101415 A1 * | 5/2005 | Sweeney | 473/407 |
| 2006/0166724 A1 * | 7/2006 | Toroussian | 463/1 |
| 2007/0265105 A1 * | 11/2007 | Barton et al. | 473/220 |
| 2008/0102972 A1 * | 5/2008 | Lindsay | 473/251 |
| 2010/0105456 A1 * | 4/2010 | Marufuji | 463/9 |
| 2010/0167809 A1 * | 7/2010 | Perlman et al. | 463/24 |
| 2010/0167816 A1 * | 7/2010 | Perlman et al. | 463/30 |

* cited by examiner

*Primary Examiner* — Pierre Eddy Elisca
*Assistant Examiner* — Shahid Kamal
(74) *Attorney, Agent, or Firm* — Michael A. Catania; Rebecca Hanovice; Sonia Lari

(57) ABSTRACT

A method, system and golf ball determine the side spin and/or back spin of a golf ball to facilitate the evaluation of a putt. In one embodiment, a system includes a golf ball and an off-board display device. The golf ball includes a golf ball body, a motion sensor disposed within the golf ball body and configured to measure acceleration of the golf ball along each of three mutually perpendicular axis, and a transmitter within the golf ball body transmits data representative of spin of the golf ball. The display device includes a receiver and a display, and the receiver receives data representative of the spin of the golf ball from the transmitter and the display is configured to provide a representation of a measure of the spin of the golf ball.

4 Claims, 3 Drawing Sheets

METHOD AND APPARATUS FOR EVALUATING A PUTT

CROSS REFERENCE TO RELATED APPLICATIONS

The present application claims priority to provisional applications bearing Application Nos. 61/052,343 and 61/052,314 filed May 12, 2008, the contents of both of which are incorporated herein in their entirety.

FIELD OF THE INVENTION

A method and apparatus are provided according to embodiments of the present invention to evaluate the putting of a golfer.

BACKGROUND OF THE INVENTION

It is desirable in many instances to evaluate the putting of a golfer. For example, a golfer, a swing coach or other golfing professional may desire to evaluate a putting technique for training and practice purposes. Additionally, club manufacturers and others may similarly desire to evaluate putting performance as part of the process of evaluating clubs. Further, golfers may like to play games that are based upon an evaluation of their putting, thereby allowing a golfer to have fun while also working on their putting.

The system uses a motion sensor, such as an accelerometer, embedded in the golf ball to monitor the forces acting on the ball as it is being putted and the subsequent motion of the ball. This information is analyzed for indications of putting quality and the data is presented to the user in a number of ways. The system of one embodiment transmits the analyzed data to an offboard display device via radio. This information may be used for putting training and practice, evaluating clubs for comparison and games.

BRIEF SUMMARY OF THE INVENTION

A method, system and golf ball are therefore provided in accordance with embodiments of the present invention in order to determine the spin of a golf ball, such as the side spin and/or back spin, in order to facilitate the evaluation of a putt. In one embodiment, a system includes a golf ball and an offboard display device. The golf ball may include a golf ball body, a motion sensor disposed within the golf ball body and configured to measure acceleration of the golf ball along each of three mutually perpendicular axes, and a transmitter disposed within the golf ball body configured to transmit data representative of spin of the golf ball. In turn, the display device may include a receiver configured to receive data representative of the spin of the golf ball from transmitter and a display configured to provide a representation of a measure of the spin of the golf ball. In this embodiment, at least one of the golf ball and the display device may include a processor configured to determine spin of the golf ball based upon the acceleration measured by the motion sensor.

The processor may be configured to determine at least one of backspin or side spin. For example, the processor may be configured to determine the side spin of the golf ball based upon a time rate of angular rotation of an acceleration vector about a vertical axis. Similarly, the processor may be configured to determine the backspin of the golf ball based upon a time rate of angular rotation of an acceleration vector about a horizontal axis.

In addition to the system described above, a method and a golf ball, including an embedded processor, are also provided in accordance with other embodiments in order to determine the spin of the golf ball and, in turn, to facilitate the evaluation of a putt.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

OVERVIEW OF THE SYSTEM

Embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Figure 1:
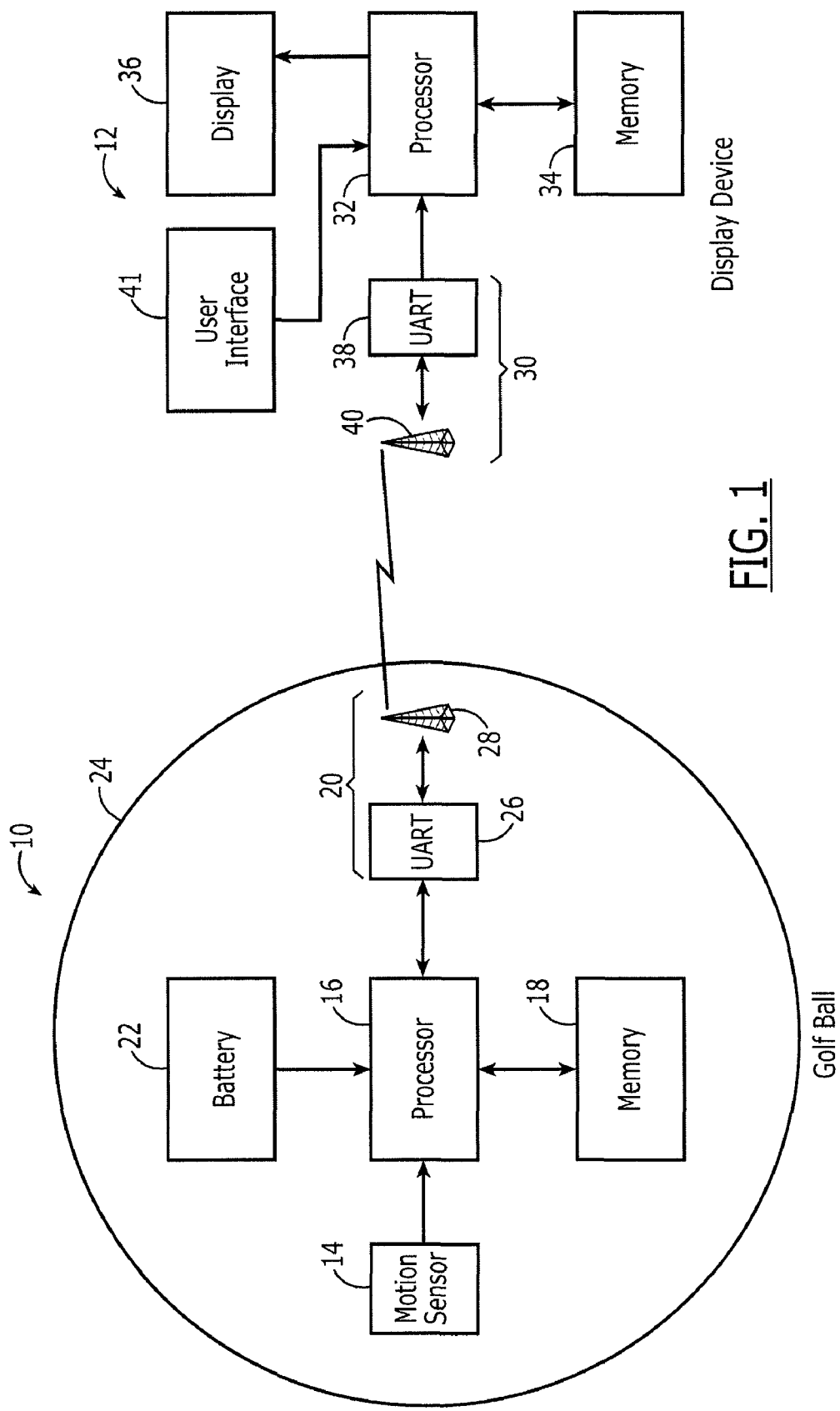
FIG. 1 is a block diagram of a system in accordance with one embodiment of the present invention.

The system consists of a modified golf ball 10 and a display device 12 configured to communicate with one another, typically in a wireless manner. The golf ball of one embodiment has a motion sensor 14, processor 16, memory 18, radio 20 and power system 22 embedded into the body 24 of the golf ball. As shown in FIG. 1, the motion sensor may be three-axis accelerometer configured to repeatedly provide a three-dimensional vector indicative of the current acceleration acting upon the ball in three orthogonal directions, e.g., the x, y and z directions. Other types of motion sensors can employed including, for example, magnetometers, if so desired. The output of the accelerometer may be provided to an analog-to-digital converter for converting the signals representative of the current acceleration to digital values which, in turn, are provided to the processor.

The processor 16 includes or is otherwise associated with a clock and, as such, associates a time with each set of acceleration values provided by the motion sensor 14 and stores the acceleration values in memory 18. By storing the acceleration values over time, the processor can also integrate the acceleration along each of the three orthogonal axes in order to determine the velocity of the golf ball 10 along each of the three orthogonal axes. The processor can further integrate the velocity along each of the three orthogonal axes in order to determine the position of the ball along each of the three orthogonal axes. As described below, the processor can further process the acceleration values and analyze the results depending upon the desired output.

The processor can also transmit the results to the offboard display device 12. In this regard, the radio of the golf ball may also include a transmitter or a transceiver and an associated antenna for providing a wireless transmission to the display device. As shown in FIG. 1, for example, the radio 20 of the golf ball may include a universal asynchronous receiver/transmitter (UART) 26 and an associated antenna 28, such as a single chip 802.15.4 low-power digital data radio, for supporting the wireless communication with the display device. As to the power system 22, the golf ball may include an onboard battery which may, in one embodiment, be wireless recharged. For example, the battery may be a CR2032 battery or the like. Alternatively, the electronics of the golf ball may operate passively with energy provided from an external source.

The display device 12 also generally consists of a radio 30, processor 32, memory 34 and a display 36, such as an LCD display. As described in conjunction with the golf ball, the radio of the display device may also include a transmitter or a transceiver and an associated antenna for receiving wireless transmissions from the golf ball. As shown in FIG. 1, for example, the radio of the display device may include a universal asynchronous receiver/transmitter (UART) 28 and an associated antenna 40 for supporting the wireless communication with the golf ball. The processor of the display device can provide for storage of the information provided by the golf ball and can appropriately drive the display in order to provide at least some of the information received from the golf ball to the user. If desired, the display device may include a user interface for permitting the user to provide input regarding the information to be presented and/or the format of the information to be presented. Further, the display device may include an interface 41, such as a USB interface, a BlueTooth interface or the like, for permitting the information provided by the golf ball and stored by the display device to be downloaded to a computer. Further, while the system of one embodiment is described herein such that the processor of the golf ball performs the analysis of the data provided by the motion sensor, the processing responsibilities can be differently divided with the processor of the display device performing some or all of the analysis.

In operation, when the processor 16 of the ball 10 detects a putting stroke, the processor measures the output of the motion sensor 14 at a predetermined rate, such as 1000 times per second, until the processor determines the motion has completed. With this data, the processor is able to make a number of measurements and draw conclusions about the putt. This information is transmitted to the display device 12 so the user can benefit from the information. Furthermore, the processor 32 in the display device can use the data to provide a historical analysis of putting, compare multiple clubs or gaming.

Methods of Measurement

Figure 2:
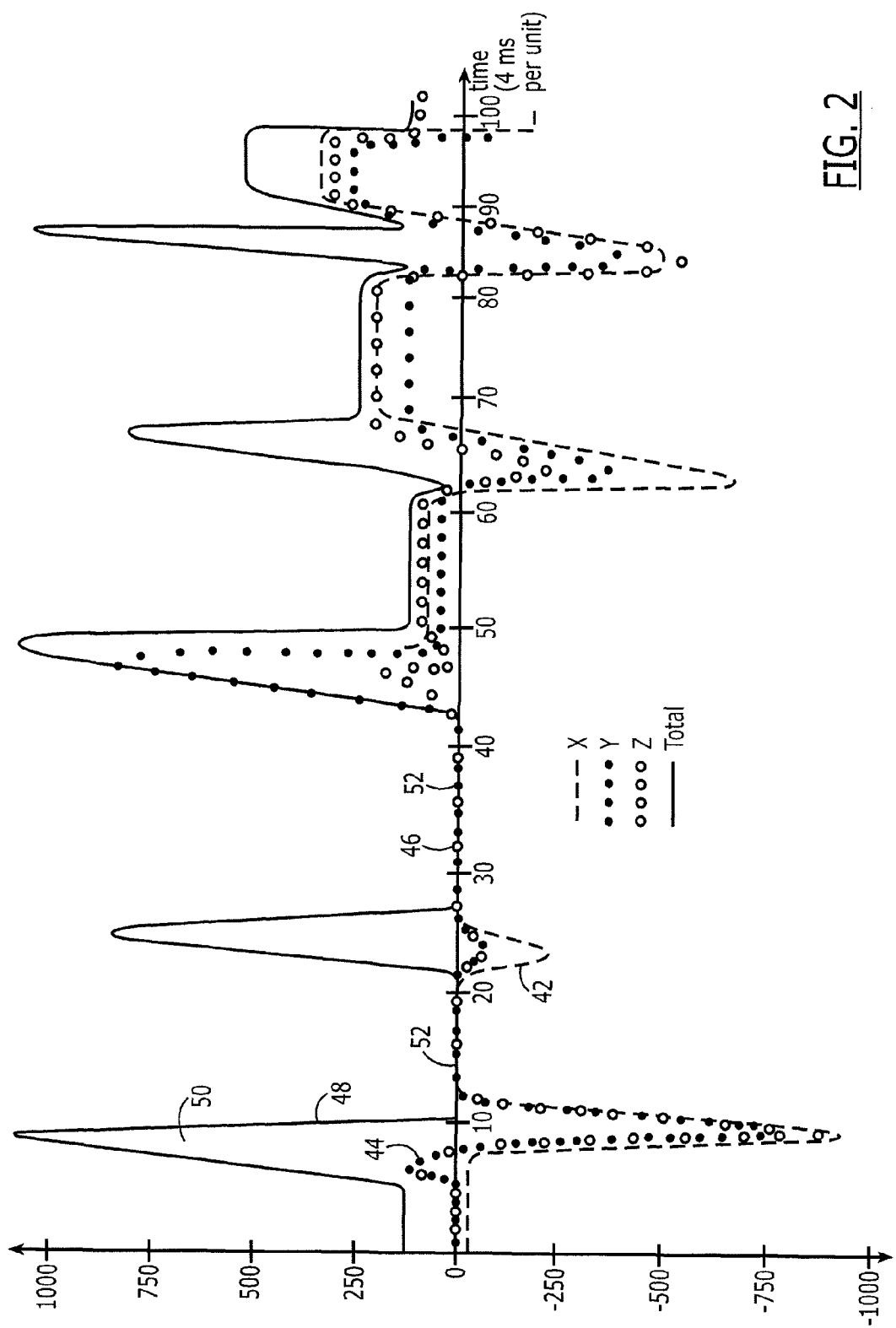
FIG. 2 is an example of a waveform produced by a motion sensor in accordance with one embodiment of the present invention.
Figure 3:
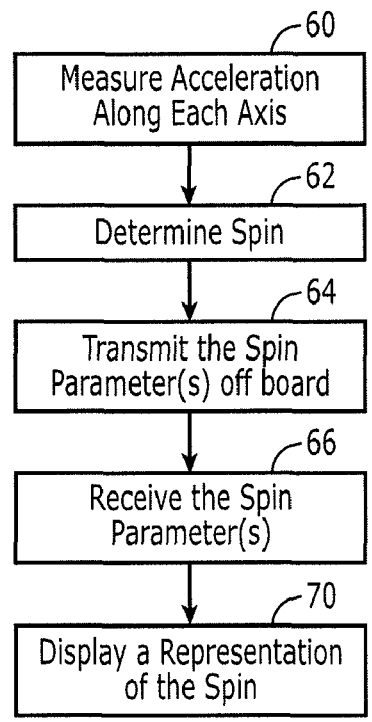
FIG. 3 is a flow chart of operations performed in accordance with embodiments of the present invention.

A putt consists of several phases, each requiring different analysis. While the ball is not in use, the system of one advantageous embodiment efficiently uses power while waiting for putting stroke. As such, prior to the detection that the ball 10 is being putted, the processor 16 samples the output of the motion sensor 14 at a predetermined, slow rate. Based upon the outputs of the accelerometers preceding club impact upon putting, the processor determines an at-rest vector that defines a coordinate system of the motion sensor and may be subsequently used as a normalizing vector for the acceleration vector measured during motion of the ball. When a strong acceleration is detected, that is, acceleration having a magnitude greater than a predefined threshold (typically, the magnitude of the total acceleration, that is the square root of $a_x^2 + a_y^2 + a_z^2$ wherein $a_x$, $a_y$ and $a_z$ are the accelerations in the x, y and z axes, respectively), the processor begins sampling the motion sensor at a predetermined, fast rate, such as 1000 times/second, and the duration and amplitude of the acceleration are examined by the processor relative to predefined thresholds to determine if this is a valid putting stroke. See block 60 of FIG. 3. In one embodiment, for example, the duration of the initial acceleration should be less than 20 ms and the magnitude of acceleration should exceed 8 g. In order to verify that the golf ball has been putted, the processor may also consider the subsequent acceleration signals to insure that the acceleration signals are indicative of a putt which concludes with a decelerating roll. Moreover, the duration and the shape of the magnitude envelope may be important, as when the ball is "pinched" against the ground, the trailing edge of the magnitude signal will elongate rather than going straight to ground. In other words, the slope of the trailing edge will be less than vertical. By way of example, the accelerometer signals indicative of a typical putt in which the magnitude of the acceleration is measured along the vertical axis and time in milliseconds is measured along the horizontal axis are shown in FIG. 2.

The lines designated 42, 44 and 46 are the actual reading from each axis of the sensor, designated the x, y and z axes, respectively. The thick line is the computed magnitude of all three axes when treated as a vector. The first spike 50 on the left side is the putting stroke. The shape of this spike indicates the nature of the impact between the ball and the club. For instance, if the slope of the descending magnitude flattens out slowly, this can indicate that the club was forcing the ball into the ground before it started moving.

Following the impact spike, the ball 10 generally enters a phase of zero magnitude indicating that the ball is in flight. While this is difficult to directly observe, nearly every putt has moments of flight. In this case, the plot shows two such segments 52; 11 to 21 and 25 to 43. During these segments, the processor 16 may monitor the output of the motion sensor 14 and determine the rotation vector representative of the acceleration due to rotation of the golf ball while airborne prior to impact with the ground. The duration and number of the flights are used to determine the "bounciness" of the ball as it is transitioning to a pure roll condition.

Each subsequent spike is caused by the ball 10 impacting the ground. During this time, the output of the motion sensor 14 is treated as a vector (direction and magnitude) that is normalized, such as by means of a Rodrigues transform, in comparison to the "at-rest" vector that was determined during the moments prior to the start of the putt. Additionally, the processor 16 may remove the effect occasioned by the rotation of the golf ball while airborne prior to impact with the ground by subtracting the rotational vector described above from the output of the motion sensor, thereby resulting in the impact acceleration vector which will be further analyzed as described below. The changes in these vectors from bounce to bounce are used to compute the backspin and sidespin placed on the ball by the club impact. See block 62 of FIG. 3. In this regard, spin is determined during the bounces since the ball and the sensor may be treated as a fixed body in a static, e.g., no rotation, state with the forces acting on the ball being gravity and its impact upon the ground. In terms of sidespin, if the acceleration vector is rotated about the normalized vertical axis from bounce to bounce, the processor can measure the side spin from one bounce to another bounce as being the change in the angle of the acceleration vector about the normalized vertical axis per unit of time (and multiplied by 60 to generate a result in revolutions per minute (RPM)). This method may also be verified by the double-integration of the acceleration, which permits the path of the ball to be traced in order to determine the side spin. For backspin, the same methods apply except that the processor is considering the rotation of the angle of the acceleration vector from one bounce to another relative to the horizontal plane.

As the ball 10 begins to roll forward, centripetal forces start to act on the motion sensor, as well as gravity. These two components combine to create a signal on each axis consisting of a sine wave attributable to gravity with an offset due to centripetal force. The frequency and duration of the sine wave can be used to measure the speed and distance the ball is traveling. In this regard, the acceleration signals as measured along each axis will produce a sine wave as the ball rotates relative to gravity. When the axis is normal to the ground, the accelerometer will sense nearly 0 g. When the axis is pointed down, the accelerometer will sense nearly 1 g and conversely when the accelerometer is pointed straight up, it will sense −1 g. If the axis is not perfectly parallel or normal to the gravity vector, the accelerometer will sense a value that is related to 1 g*cos(tilt angle (e.g., angle relative to the gravity vector)).

As such, when the ball 10 is rotating, the acceleration signals as measured along each axis will be a sine wave. For the purposes of measuring RPM and distance rolled, it is not necessary to measure the amplitude of the sine wave just the frequency. If a ball rolls 10 feet, it would be expected that the number of sine waves would equal 120"/(1.68"*pi). Conversely, if the number of sine waves is known and is denominated as wavecnt, you can work out the rolling distance by: (1.68"*pi)*wavecnt. Once the distance is determined, the processor 16 can determine the speed by dividing the distance by the time taken to traverse the distance. This only works for the portion of the putt where the ball is rolling. Prior to that, when the ball is sliding, the processor may double integrate the acceleration vectors to compute the distance. Since the motion sensor 14 may not be at the precise center of gravity, centripetal force will add an offset to the sine wave. As such, the golf ball may include a digital high pass filter to subtract this DC offset from the signal.

If the phase relationship of the sine waves between the three axes is constant, then the ball 10 is rolling in a straight line. However, measuring the change in the phase relationship makes it possible to compute the actual rolling path of the ball. In this regard, the phase change between axes is only present if the ball starts to roll along a different axis. For every possible rolling axis, the sensor axes will each demonstrate a different phase. This is because as the ball rolls, the accelerometer signal along an axis will "peak" at a different time in the ball roll cycle. If the relative phases are compared at the beginning of the roll versus the ending of the roll, this phase relationship will change if the ball has changed its rolling axis. By measurement of these changes, the processor 16 can track the path of the ball.

Stated differently, as a ball rolls along a straight path, each axis of the accelerometer will experience a fixed sine wave along with an attendant offset due to centripetal force. The phase of the sine wave for each axis will be fixed as well since the "path" of each axis is consistent. However, as the ball turns, the phase shifts since each axis starts to follow a new rotational path. For instance, if the ball is rolling about the z-axis, the y-axis and x-axis will be 90 degrees out of phase. As the ball starts to change its direction this phase will change in a predictable manner. By monitoring the change in phase of the sine waves along each axis, the processor can determine that the ball deviated from a straight path and can determine the actual path along with the ball now rolls.

The processor 16 can alternatively or additionally track the path of the ball 10 through double-integration of the acceleration values as well. The only issue with this technique is that even the smallest measurement errors can add up very quickly. Since integration is the adding of measurements, there is no computational opportunity to eliminate error. Therefore this technique is generally best used for short durations (determined by the quality and number of measurements) and its accuracy must not be overestimated. Indeed, its most useful output may be to identify changes in direction rather than determining an absolute position.

The processor 16 may also employ single integration to determine the speed of the ball, but it may not be as accurate as examining the frequency of the rolling sine waves. During the initial putt skid/bounce sequence, it can be used to make gross measurements of the speed.

Once the spin is determined, the processor 16 of the golf ball 10 may provide the spin to the display device 12 for presentation to the user, either alone or in comparison to historical information. Further, additional parameters, such as skid time, number of bounces, etc. may also be provided in some embodiments. See blocks 64, 66 and 68 of FIG. 3.

Method of Scoring a Putt

The following graphic describes a mathematical method that may be employed by the processor 32, such as the processor of the display device 12, to combine the measured values of a putt into a useful score. In this regard, the processor of one embodiment is configured to determine each of the parameters based upon the signals provided by the motion sensor 14 and to then combine the parameters (once scaled and/or weighted, if so desired) in accordance with a predefined algorithm. This is an example method as other derivations are useful as well. In the illustrated scoring technique, the back spin and side spin can be determined as described above. The skid time is the time, such as the number of milliseconds, where the ball is showing zero gravity. In some cases the ball may be rotating enough while it is skidding (such as after the second bounce) that some centripetal force may be measured. In this case, it may be better to measure the skid time as the time from the putt impact to the final bounce. Conversely, a bounce is defined as a short duration (e.g., <20 ms) spike such that the bounce count is the number of bounces taken by the golf ball prior to rolling, while bounce energy is the area under the curve defined by the magnitude of the acceleration vector. Finally, velocity may be determined by integrating acceleration with the value of velocity that is displayed being the initial or maximum velocity, the average velocity or any other velocity value that is desired. In the illustrated embodiment and as noted below, U appropriately scales each variable to within a unitless range of 0 to 100, while W appropriately weights each variable depending upon its perceived importance to the resulting score.

| Scoring | Variables | Method |
| --- | --- | --- |
| $S_Z$ | Back or Top Spin | $SCORE_{PUTT} = S_Z * U_{SZ} * W_{SZ} +$ |
| $S_Y$ | Side Spin | $S_Y * U_{SY} * W_{SY} +$ |
| $T_{SKID}$ | Skid Time | $T_{SKID} * U_{TS} * W_{TS} +$ |
| $B_{COUNT}$ | Bounce Count | $B_{COUNT} * U_{BC} * W_{BC} +$ |
| $B_{ENERGY}$ | Bounce Energy | $B_{COUNT} * U_{BC} * W_{BC} +$ |
| V | Velocity (optional) | $V * U_V * W_V$ |
| SCORE | 1 to 100 - 100 is perfect | |

Notes
Each value of U scales its respective value (0 to 100)
W is an integer that represents the value or weight of the variable
Not shown is the score is divided by the sum of W to get a score (0 to 100)

Applications

Figure 4:
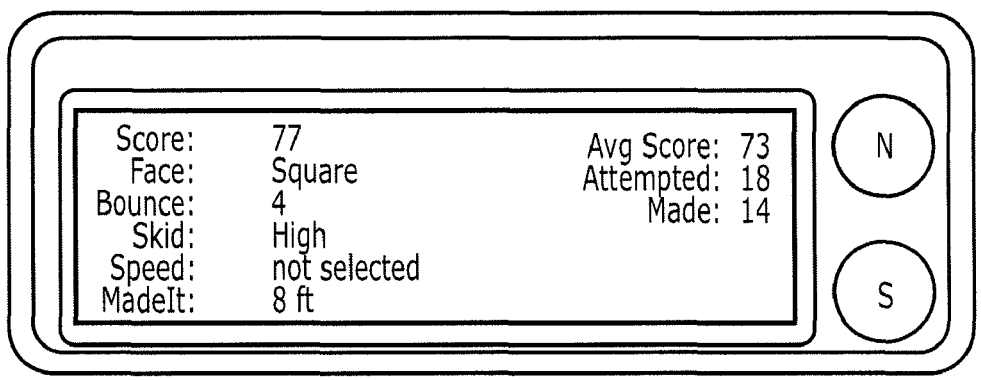
FIG. 4 is an example output of a practice/training aid application supported by a system in accordance with embodiments of the present invention.
Figure 5:
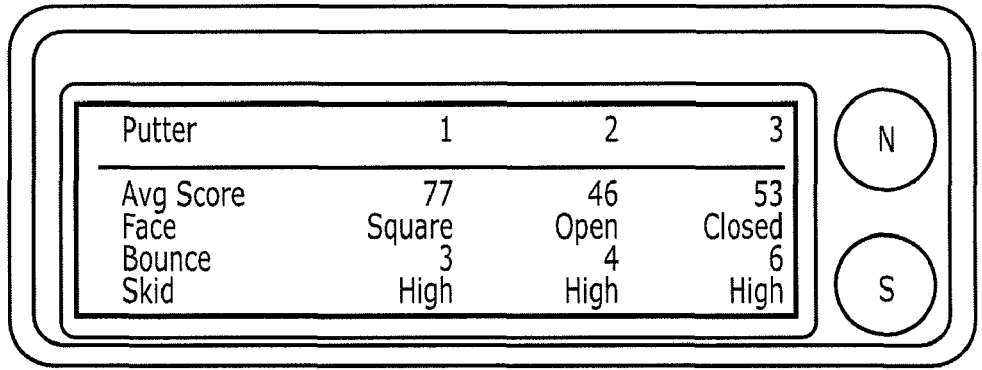
FIG. 5 is an example output of a club comparison application supported by a system in accordance with embodiments of the present invention.

The output of the display device 12 is pictured in FIGS. 4 and 5 in accordance with two applications. Other applications such as gaming are similarly within the scope of the present invention. The first application shown in FIG. 4 is a practice/ training aid that gives detailed information about each putt and summary information about the practice session which is comprised of multiple putts, i.e., 18 putts. In order to convert the skid into more readily understandable information, predefined numerical ranges associated with low, medium and high skid may be defined and the resulting skid value may be classified accordingly. In addition, the face angle is measured as a consequence of the side spin. If there is very little sidespin, such as less than a predefined value, the face is considered square. If the ball is spinning clockwise with sidespin greater than the predefined value, the face is open and if the ball is spinning counterclockwise with the sidespin greater than the predefined value, the face was closed. The loft of the club at impact is measured as a combination of the backspin and the skid duration. The longer a ball skids divided by the ball velocity, the more positive loft on the club. Also, if the ball has a lot of backspin (RPM) then more positive loft was applied. The converse is true as well except that if the negative loft is greater than 2 or 3 degrees, the ball is "pinched" against the ground causing the putt impact spike to be shaped more like a descending ramp on the trailing edge rather than a sharp cliff.

Different applications may, of course, produce different outputs. For example, FIG. 5 depicts the result provided by a display device 12 of a club comparison application that allows the user to understand the relative strengths and weaknesses of several clubs.

Each of the foregoing values may be determined by the processor 16 of the golf ball 10 or, in some embodiments, certain values may be determined by the processor of the golf ball and other values are determined by the processor 32 of the display device 12. In any event, the processor of the golf ball and the display device may perform the above-described method under control of a computer program product that may be stored, for example, by the associated memory device 18, 34. For example, one or more of the procedures described above may be embodied by computer program instructions. As will be appreciated, any such computer program instructions may be loaded into the memory and, in turn, the associated processor to produce a machine, such that the instructions which execute on the processor create means for implementing the functions specified in the flowcharts block (s) or step(s). These computer program instructions may also be stored in a computer-readable memory that can direct a processor or other programmable apparatus to function in a particular manner, such that the instructions stored in the computer-readable memory produce an article of manufacture. The computer program instructions may also be loaded onto a processor or other programmable apparatus to cause a series of operational steps to be performed on the processor or other programmable apparatus to produce a computer-implemented process.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A system for evaluating a spin of a moving golf ball that is struck with a golf club, the system comprising:
a golf ball comprising:
a golf ball body;
a motion sensor disposed within the golf ball body and configured to measure acceleration of the golf ball along each of three mutually perpendicular axis;
a processor disposed within the golf ball body and configured to determine spin of the golf ball based upon the acceleration measured by the motion sensor, the processor further configured to determine the backspin of the golf ball based upon a time rate of angular rotation of an acceleration vector about a horizontal axis; and
a transmitter disposed within the golf ball body configured to transmit data representative of spin of the golf ball; and
a display device comprising:
a receiver configured to receive data representative of the spin of the golf ball from transmitter;
a display configured to provide a representation of a measure of the spin of the golf ball, wherein at least one of the golf ball and the display device comprises a processor configured to determine the spin of the golf ball based upon the acceleration measured by the motion sensor.

2. The system according to claim 1 wherein the processor is further configured to determine the side spin of the golf ball based upon a time rate of angular rotation of an acceleration vector about a vertical axis.

3. The system according to claim 1 wherein the processor is further configured to determine a skid time or a bounce count.

4. The system according to claim 1 wherein the processor is configured to determine a score based upon at least the spin of the golf ball.

* * * * *